(12) United States Patent
Mattey et al.

(10) Patent No.: US 8,288,089 B2
(45) Date of Patent: Oct. 16, 2012

(54) PARTICLE BINDING

(75) Inventors: Michael Mattey, Hertfordshire (GB); Robert Ivan Wilkinson, Hertfordshire (GB)

(73) Assignee: Fixed Phage Limited, Mauchline, East Ayrshire (GB)

( * ) Notice: Subject to any disclaimer, the term of this patent is extended or adjusted under 35 U.S.C. 154(b) by 825 days.

(21) Appl. No.: 12/158,092

(22) PCT Filed: Dec. 22, 2006

(86) PCT No.: PCT/GB2006/004907
§ 371 (c)(1),
(2), (4) Date: Sep. 8, 2008

(87) PCT Pub. No.: WO2007/072049
PCT Pub. Date: Jun. 28, 2007

(65) Prior Publication Data
US 2009/0053789 A1    Feb. 26, 2009

(30) Foreign Application Priority Data
Dec. 22, 2005   (GB) .................................. 0526176.3

(51) Int. Cl.
*C12Q 1/70* (2006.01)
(52) U.S. Cl. .......................... 435/5; 424/204.1; 424/93.6
(58) Field of Classification Search ........................ None
See application file for complete search history.

(56) References Cited

U.S. PATENT DOCUMENTS
7,078,001 B2 * 7/2006 Jorgensen ................ 422/186.05

FOREIGN PATENT DOCUMENTS

| | | | |
|---|---|---|---|
| DE | 2646798 | A1 | 4/1978 |
| DE | 10038774 | A1 | 12/2001 |
| EP | 0995495 | A | 4/2000 |
| EP | 1254971 | A | 11/2002 |
| WO | WO 02087876 | A | 11/2002 |
| WO | WO 03/093462 | * | 11/2003 |
| WO | WO 03093462 | A | 11/2003 |
| WO | WO 2006092629 | A | 9/2006 |

OTHER PUBLICATIONS

Ida J-I et al: "Surface modification of a ceramic membrane by the SPCP-CVD method suitable for enzyme immobilization" Journal of Electrostatics, Amsterdam, NL, vol. 49, No. 1-2, May 2000.
Yamamoto Hideo et al: "Immobilization of a bio-catalyst (enzyme) on a ceramic surface treated by the SPCP-CVD method" Adv Powder Technol; Zeist, Netherlands, vol. 7, No. 4, 1996.
Ida J-I et al: "Immobilization of a glucoamylase on ceramic membrane surfaces modified with a new method of treatment utilizing SPCP-CVD" Biochemical Engineering Journal 2000 Switzerland, vol. 5, No. 3, 2000.
Seto Fusako et al: "Surface grafting of poly(vinylamine) onto poly-(ethylene) film by corona discharge-induced grafting" J. Appl. Polym. Sci.; vol. 72, No. 12, Jun. 20, 1999.
International Preliminary Report on Patentability dated Jun. 24, 2008.
International Search Report issued regarding International Application No. PCT/GB2006/004907 (Feb. 29, 2008).
Written Opinion issued regarding International Application No. PCT/GBf2006/004907 (Feb. 29, 2008).

* cited by examiner

*Primary Examiner* — Benjamin P Blumel
(74) *Attorney, Agent, or Firm* — Thompson Hine LLP (57) ABSTRACT

A method of binding bacteriophage to particles. The method comprising the steps of exposing the particles to an electrical discharge and then mixing the activated particles with the bacteriophage. The bacteriophage are then bound to the particles.

17 Claims, 7 Drawing Sheets

FIG. 4
Plaques from beads after immobilisation and washing

FIG. 5
Bacteriophages removed by washing

PARTICLE BINDING

The present invention relates to a method of binding viruses such as bacteriophage to a substrate and an apparatus for binding viruses to a substrate.

Bacteriophage are viruses which infect bacteria. They have been used for some years as cloning vectors in molecular genetics because of their capability of carrying a nucleic acid encoding a protein which is then expressed in an infected bacterium.

WO03/093462 discloses that bacteriophage may also be used as "antibiotics" in a medical context in the treatment or prevention of bacterial infections and/or contamination, provided that the bacteriophage are immobilised on a substrate. Bacteriophage are desirable for use in this context in view of the growing prevalence of bacterial resistance to conventional antibiotic compositions.

WO03/093462 reports generally on methods for immobilising bacteriophage on substrates in general. However, it has now been determined that it would be desirable to bind viruses such as bacteriophage to particles in order to utilise them more effectively. The present invention therefore seeks to address this need.

According to one aspect of the present invention, there is provided a method of binding virions to a plurality of particles comprising the steps of:
(a) exposing the particles to an electrical discharge in order to activate the particles; and
(b) mixing the activated particles with the virions such that the virions become bound to the particles.

According to another aspect of the present invention, there is provided a method of binding virions to a plurality of particles comprising the steps of:
(a) using an electrical discharge in order to activate the particles; and
(b) mixing the activated particles with the virions such that the virions become bound to the particles.

Preferably, step (a) comprises the step of exposing the particles to the electrical discharge.

Alternatively, step (a) comprises the step of exposing a medium to the electrical discharge and mixing the medium with the particles.

Conveniently, the method further comprises the step of, prior to step (a) attracting the particles to a conveyor and moving the conveyor in order to bring the particles into proximity with the electrical discharge.

Preferably a portion of the conveyor is in contact with a source of the particles.

Advantageously, the step of attracting the particles to the conveyor comprises the step of charging the conveyor so as to attract the particles to the conveyor.

Conveniently, step (a) comprises reversing the charge on the particles and removing the particles' attraction to the conveyor.

Preferably, the conveyor comprises a rotatable drum.

Alternatively, the conveyor comprises a movable conveyor belt.

Advantageously, the electrical discharge has a perimeter and an aperture therethrough.

Conveniently, the perimeter defines a plane which is substantially horizontal and step (a) comprises the step of dropping the particles through the aperture in the electrical discharge.

Alternatively, step (a) comprises projecting the particles through the aperture in the electrical discharge.

Preferably, the particles are projected by an air jet.

Conveniently, step (a) comprises projecting the particles or a medium through the electrical discharge.

Preferably, step (a) comprises projecting the particles through the electrical discharge.

Advantageously, step (a) further comprises the step of imparting a helical flow pattern on the particles prior to projecting the particles through the electrical discharge.

Alternatively, step (a) comprises projecting a medium through the electrical discharge.

Conveniently, step (a) further comprises the step of, after projecting the particles through the electrical discharge, mixing the medium with the particles.

Preferably, the medium is a gas.

Advantageously, the gas comprises oxygen, preferably wherein the gas is air.

Alternatively, the gas is inert, preferably comprising nitrogen.

Advantageously, the particles are mixed with the virions in a solution.

Conveniently, the method further comprises the step (c) of extracting the particles from the solution.

Preferably, the particles are beads.

Advantageously, the virions are bacteriophage.

According to a further aspect of the present invention, there is provided an apparatus for binding virions to particles comprising:
a moveable conveyor;
a charging device capable of generating a charge on the conveyor for attracting the particles;
an electrical discharge device capable of generating an electrical discharge adjacent to the conveyor; and
a vessel for storing the virions, the conveyor being positioned relative to the electrical discharge device and the vessel for transporting particles through the electrical discharge and into the vessel.

Conveniently, the conveyor comprises a rotatable drum.

Alternatively, the conveyor comprises a movable conveyor belt.

Preferably, the vessel for storing virions comprises a solution of the virions.

Advantageously, the apparatus further comprises a receptacle for storing the particles and distributing the particles on the conveyor.

According to another aspect of the present invention, there is provided an apparatus for binding virions to particles comprising;
an electrical discharge device capable of generating an electrical discharge having a perimeter and an aperture therethrough;
conveying means for conveying the particles through the aperture of the electrical discharge; and
a vessel for storing virions and located for receiving particles conveyed through the aperture of the electrical discharge.

According to a further aspect of the present invention, there is provided an apparatus for binding virions to particles comprising;
an electrical discharge device capable of generating an electrical discharge;
conveying means for conveying the particles or a medium through the electrical discharge; and
a vessel for storing virions and located for receiving the particles.

Conveniently, the conveying means comprise a projecting device for projecting the particles or the medium through the electrical discharge or aperture therein.

Preferably, the projecting device is capable of generating a jet of air for transporting the particles through the electrical discharge or aperture therein.

Alternatively, the electrical discharge defines a plane which is substantially horizontal and the conveying means comprises gravity.

Advantageously, the virions are bacteriophage.

Conveniently, the particles are beads.

Preferably, the apparatus comprises a first delivery mechanism for delivering the particles.

Conveniently, the first delivery mechanism is adapted to impart helical flow on the particles as they are delivered, preferably wherein the apparatus comprises an axially extending treatment chamber, the first delivery mechanism having an axis for delivering the particles which does not intersect with the axis of the treatment chamber.

Advantageously, the apparatus further comprises a second delivery mechanism for delivering the medium.

Conveniently, the second delivery mechanism is located for delivering the medium upstream of the region in which the electrical discharge device is capable of generating the electrical discharge, such that, in use, the medium is conveyed through the electrical discharge.

Preferably, the first delivery mechanism is located for delivering the particles downstream of the region in which the electrical discharge device is capable of generating the electrical discharge such that, in use, the particles mix with the medium after the medium is conveyed through the electrical discharge.

Advantageously, the first delivery mechanism is located for delivering the particles upstream of the region in which the electrical discharge device is capable of generating the electrical discharge such that, in use, the particles are conveyed through the electrical discharge.

Conveniently, the apparatus further comprises a fluidizer for generating an aerosol of particles.

Preferably, the fluidizer comprises means to aerate the particles and means to agitate the particles.

Advantageously, the electrical discharge device comprises a mesh electrode.

Alternatively, the electrical discharge device comprises a funnel-shaped electrode.

Conveniently, the electrical discharge device comprises an annular electrode.

In some embodiments, the electrical discharge has a perimeter and an aperture therethrough.

Preferably, the perimeter of the electrical discharge defines a plane which is substantially horizontal and the conveying means comprises gravity.

Advantageously, the apparatus comprises a plurality of electrical discharge devices capable of generating an electrical discharge and the conveying means is for conveying particles or a medium through each electrical discharge sequentially.

In this specification, the term "upstream" when used in relation to an electrical discharge means that there is provision for a flow of a medium and/or particles through the electrical discharge and the location is such that the medium and/or particles will pass from that location to the electrical discharge. Conversely, the term "downstream" when used in relation to an electrical discharge means that there is provision for a flow of a medium and/or particles through the electrical discharge and the location is such that the medium and/or particles will pass away from the electrical discharge.

The present invention is not limited to any particular type of electrical discharge. Examples of electrical discharges that may be used include glow discharges (i.e. a low current discharge at low pressure); arc discharges (i.e. high current, low voltage discharges and corona discharges (i.e. a discharge at around atmospheric pressure). Also included within the scope of the invention are arrangements whereby the source of electrons for a discharge comes from electromagnetic radiation, for example, radio waves, microwaves or laser light. It is to be understood, however, that corona discharge is the preferred form of electrical discharge.

In order that the present invention may be more readily understood, and so that further features thereof may be appreciated, embodiments of the invention will now be described, by way of example, with reference to the accompanying drawings in which.

Figure 1:
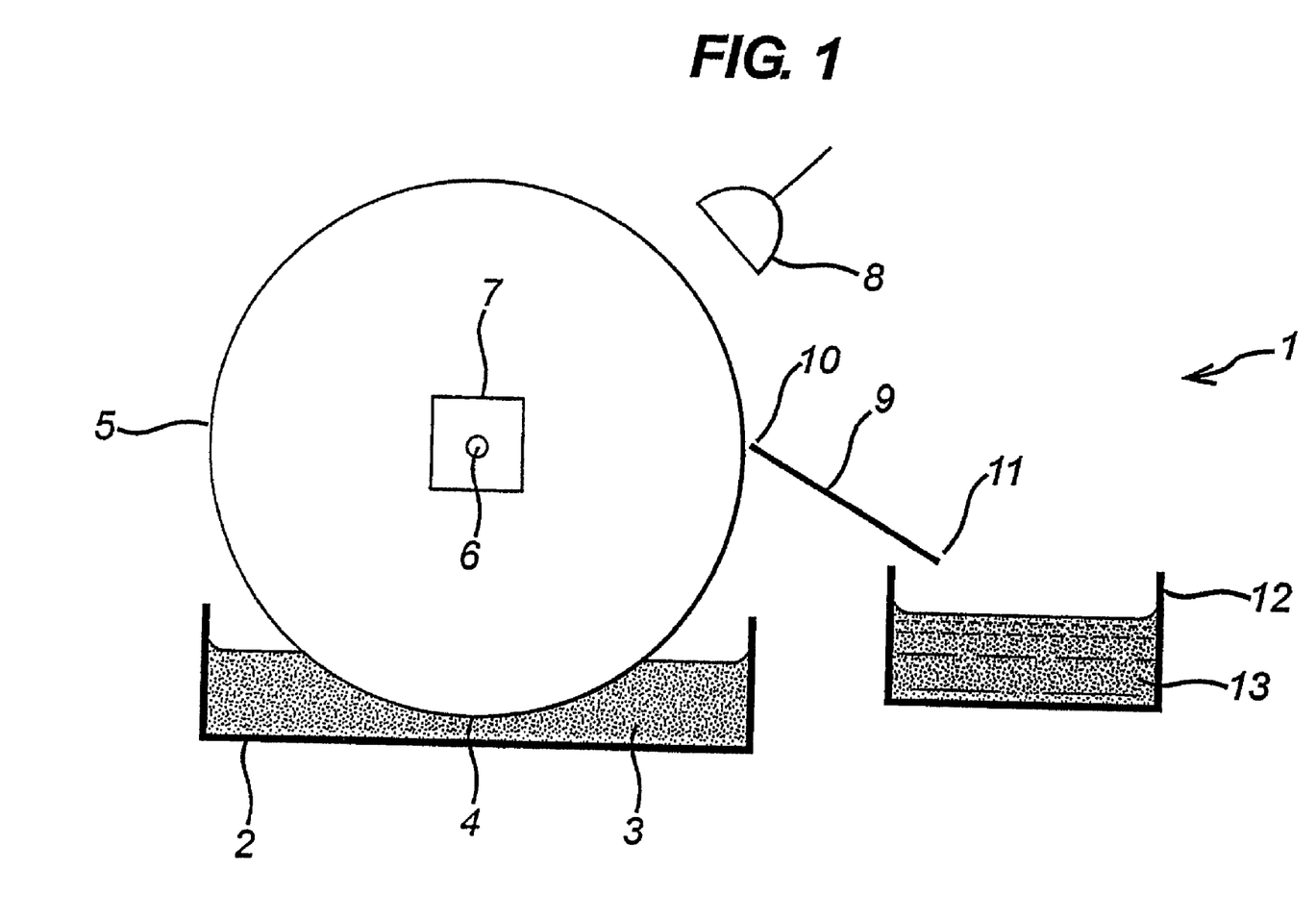
FIG. 1 is a schematic view of an apparatus in accordance with one embodiment of the present invention.
Figure 2:
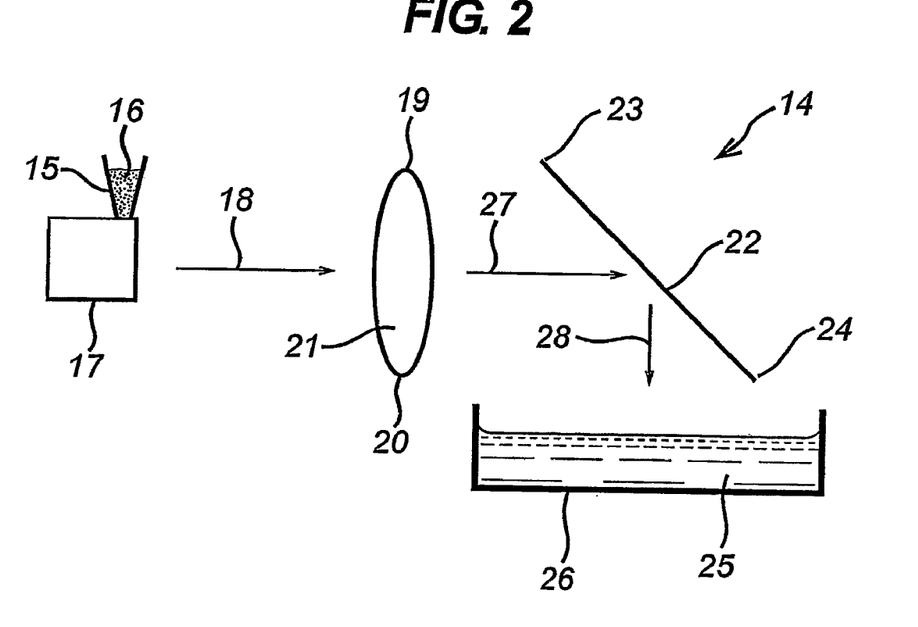
FIG. 2 is a schematic view of an apparatus in accordance with another embodiment of the present invention.
Figure 3:
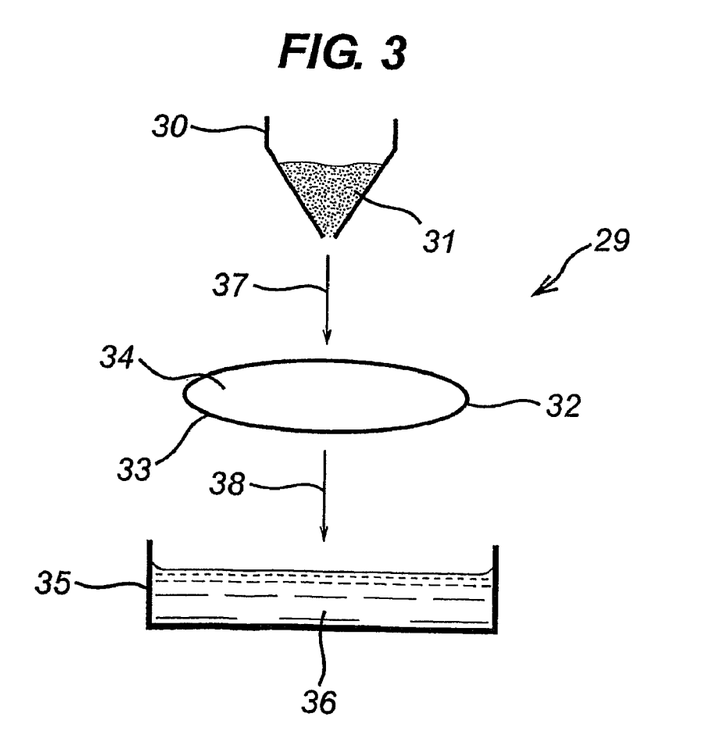
FIG. 3 is a schematic view of an apparatus in accordance with a further embodiment of the present invention.
Figure 4:
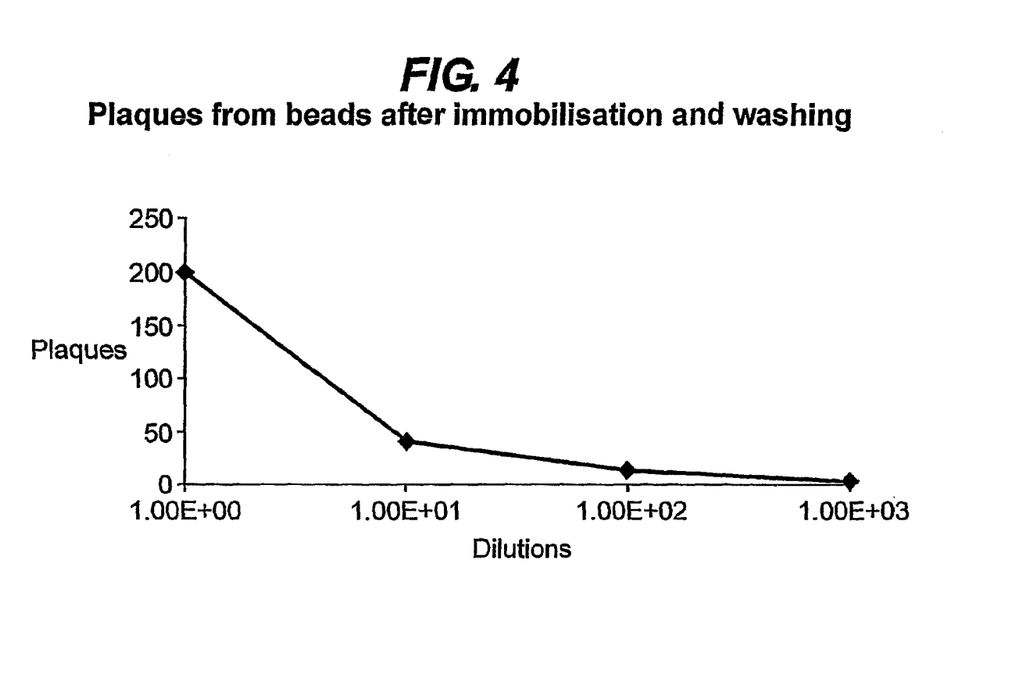
FIG. 4 is a graph showing the determination of the amount of bacteriophage bound to beads treated by a method in accordance with one embodiment of the present invention.

Referring to FIG. 1 an apparatus 1 for binding bacteriophage to beads is shown. The apparatus 1 comprises a receptacle 2 containing a supply of beads 3. The receptacle 2 has an open top and the lower part 4 of a drum 5 sits within the receptacle 2 such that the surface of the lower part or of the drum 5 is in contact with the beads 3. The drum 5 is mounted on an axle 6 which is motorised and capable of rotating the drum 5 about the axle at a constant rate in a clockwise direction. Thus the drum 5 has an ascending side on the left of FIG. 1 and a descending side on the right of FIG. 1. A charging device 7 is also provided in connection with the drum 5 and is capable of charging the surface of the drum 5 so as to attract the beads 3 to the surface of the drum 5 electrostatically.

A corona discharge device 8 is located adjacent to the upper surface of the drum 5, on the descending side of the drum 5, when it is in rotation about the axle 6. When activated, the corona discharge device 8 generates a corona discharge effective on the surface of the drum 5.

Beneath the corona discharge device 8 is provided a rectangular guide plate 9, which is fitted at an angle to the horizontal. The upper edge 10 of the guide plate 9 lies flush with the surface of the drum 5, at the same level as the axle 6.

Beneath the lower edge 11 of the guide plate 9 is provided a mixing vessel 12 comprising a solution 13 containing bacteriophage.

In use, the axle 6, and thus the drum 5, is rotated in a clockwise direction. The charging device 7 is activated so as to charge the surface of the drum 5. Consequently, the beads 3 are progressively attracted to the surface of the lower part 4 of the drum 5 and are carried by the rotation of the drum 5 over the top of the drum 5 and then towards the corona discharge device 8.

Figure 6:
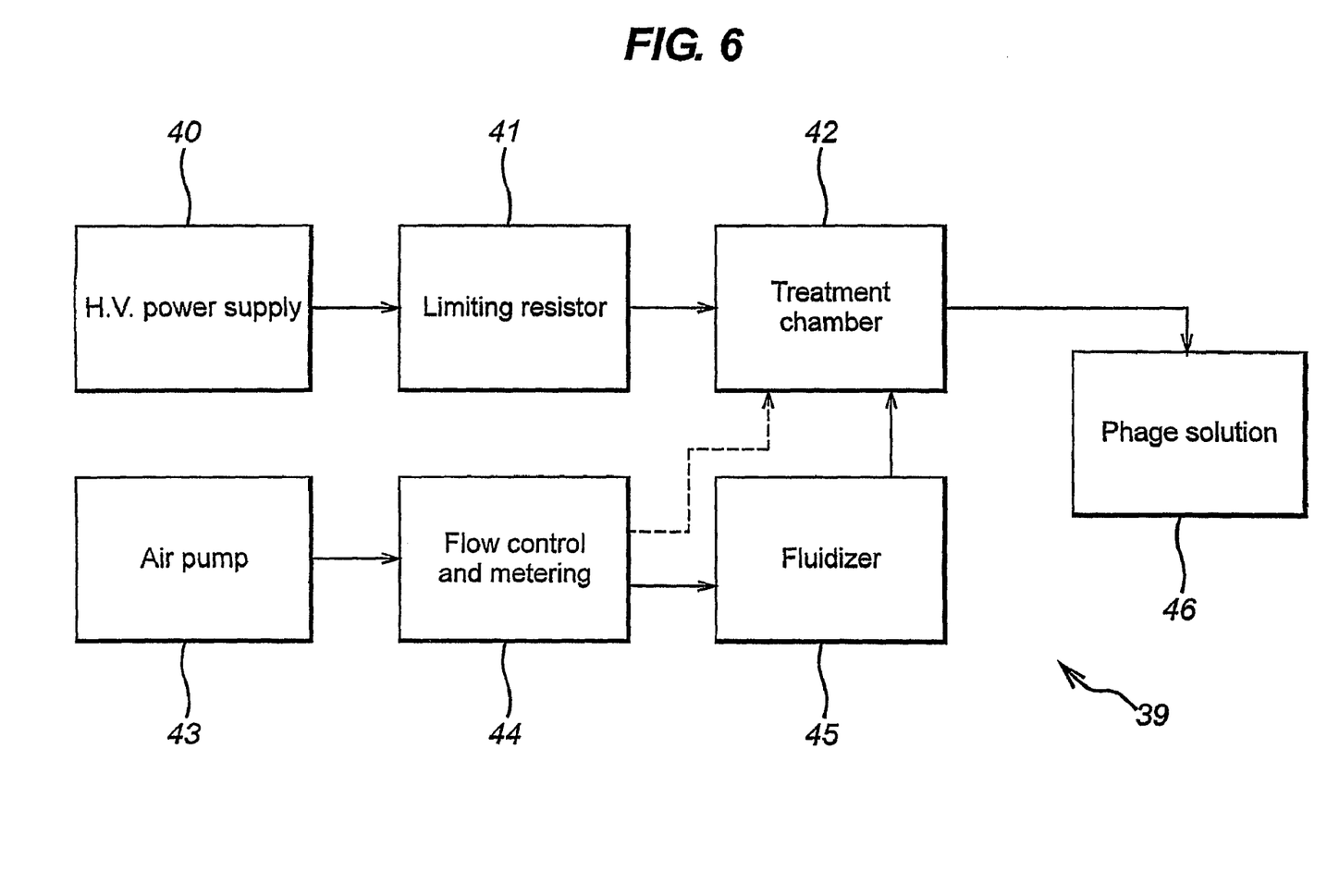
FIG. 6 is a block diagram of an embodiment of the present invention.

When the beads 3 pass adjacent to the corona discharge device 8, two operations occur. Firstly, the beads 3 are activated by the production of free radicals on their surface. Secondly, the charge of the beads 3 is changed which releases the beads 3 from attraction to the surface of the drum 5. Accordingly, as the drum 5 continues to rotate, gravity causes the beads 3 to fall from the surface of the drum 5 and onto the upper edge 10 of the guide plate 9. Under the action of gravity, the beads 3 slide down the guide plate 9 and drop from the lower edge 11 thereof into the bacteriophage solution 13.

It is to be appreciated that the movement of the beads from the time at which they are adjacent to the current discharge device 8 until the time that they enter the bacteriophage solution 13 is less than one minute and is typically only a few seconds. When the activated beads 3 come into contact with the bacteriophage in the solution 13, they bind the bacteriophage via the free radicals on the surface of beads 3. To some extent, the part of the bacteriophage to which the bead binds is random but the greater density of the heads of the bacteriophage means that binding normally occurs via the bacteriophage head. In some cases, the bacteriophage bind the beads in such a way so as to obscure the site at which the bacteriophage bind to bacteria. However, such occurrences are relatively rare and do not greatly affect the overall activity of the resulting bound bacteriophage.

After the required number of beads 3 has been activated and transported to the vessel 12, the beads are removed from the solution 13 by filtration and are dried at room temperature. The resulting beads 3 thus have bacteriophage bound to them.

In this embodiment, the apparatus 1 comprises a drum 5. However, in variants of this embodiment, the drum 5 is replaced with a conveyor belt which moves about two or more rollers. In these variants, the guide plate 9 need not be provided because the conveyor, itself, can be located such that part of it stretches above the vessel 12 containing the bacteriophage solution 13. Thus after the beads 3 have been activated by the corona discharge, their attraction to the conveyor is released and they fall directly into the vessel 12 containing the bacteriophage solution 13.

Referring to FIG. 2, another embodiment of the present invention is shown. An apparatus 14 for binding bacteriophage to beads comprises a hopper 15 containing the beads 16. Beneath the hopper 15 is provided a fan system 17 which is capable of projecting a jet of air in the direction of the arrow 18, taking with it beads 16 from the hopper 15. In the path of the arrow 18 is provided a corona discharge device 19 capable of generating a corona discharge in the shape of an annulus. Thus the corona discharge has a perimeter 20 and an aperture 21 therethrough. The perimeter 20 defines a plane which is vertical.

In one embodiment, the corona discharge device 19 comprises a circular outer electrode, which forms the perimeter 20 and a wire (not shown) which forms an inner electrode. The wire passes through the centre of the outer electrode, at right angles to the plane defined by the perimeter 20. A dielectric barrier is provided on the inner surface of the outer electrode. The corona discharge is formed between the inner and outer electrodes. In alternative embodiments, however, the inner electrode takes the form of a circular disc or annulus, of smaller diameter than the outer electrode and lying concentrically within the outer electrode. In these embodiments, the corona discharge is, again, formed between the inner and outer electrodes. The provision of such corona discharge devices is disclosed in, for example, U.S. Pat. No. 4,656,010, U.S. Pat. No. 4,999,998 and U.S. Pat. No. 4,079,260 each of which is incorporated herein by reference.

On the other side of the corona discharge device 19 is provided a back plate 22 which is positioned at an oblique angle to the vertical such that its upper edge 23 is closer to the corona discharge device 19 than its lower edge 24. Beneath the back plate 22 is provided a mixing vessel 25 containing a solution of bacteriophage 26.

In use, the fan system 17 is activated so as to project a jet of air in the direction of the arrow 18. At the same time, the beads 16 are released from the hopper 15 into the jet of air and are thus blown in the direction of the arrow 18 through the aperture 21 in the corona discharge generated by the corona discharge device 19. As the beads 16 pass through the corona discharge, they are activated so that free radicals are formed on the beads' surface. The beads 16 continue past the corona discharge in the direction of the arrow 27 and impinge upon the back plate 22 where they bounce off downwardly in the direction of the arrow 28. Subsequently the beads 16 fall into the vessel 25 where they come into contact with the bacteriophage in the solution 26. When the beads 16 contact the bacteriophage 26, the bacteriophage bind to the beads 16 via the free radicals on the beads' surface, and the beads are removed from the solution, as described in the previous embodiment.

Referring to FIG. 3, a further embodiment of the present invention is shown. An apparatus 29 for binding bacteriophage to beads comprises a hopper 30 containing a supply of beads 31. Beneath the hopper 30 is provided a corona discharge device 32 which is capable of generating a corona discharge in the form of an annulus. Thus the corona discharge has a perimeter 33 and an aperture 34 therethrough. The perimeter defines a plane which is positioned to be horizontal. Beneath the corona discharge device 32 is provided a mixing vessel 35 containing a solution 36 of bacteriophage.

In use of the apparatus 29, beads 31 are released from the hopper 30 and fall under the action of gravity in the direction of the arrow 37. The corona discharge device 32 is activated to produce the corona discharge and the beads fall through the aperture 34 in the corona discharge. As the beads 31 pass through the corona discharge, they are activated so as to have free radicals on their surface.

The activated beads 31 continue to fall in the direction of the arrow 38 under the action of gravity. The activated beads 31 thus fall into the vessel 35 and come into contact with the bacteriophage in the solution 36.

The bacteriophage in the solution 36 bind to the beads 31 via the free radicals on the beads' surface and the beads 31 are subsequently separated from the solution 36 as described in the previous embodiments.

Further embodiments of the present invention will now be described with reference to the block diagram shown in FIG. 6, which shows the components of apparatuses for binding bacteriophage to beads. As is shown in FIG. 6 an apparatus 39 comprises a high voltage power supply 40 which is linked via a current limiting resistor 41 to a high voltage electrode (not shown) in a treatment chamber 42. The current limiting resistor 41 is operable to vary the discharge energy when the high voltage electrode sparks to a ground electrode (not shown) in the treatment chamber 42. For small scale systems, the required voltage is typically of the order of a few kilo volts to tens of kilo volts. An air pump 43 is also provided and is in fluid communication with flow control means 44 for controlling and metering the flow of air from the air pump 43. The flow control means 44 is in fluid communication with a fluidiser 45 which also contains a supply of beads (not shown). The fluidiser 45 is capable of producing an aerosol of the beads. The fluidiser 45 is in fluid communication with the treatment chamber 42 and the treatment chamber 42 is, in turn, in fluid communication with a phage solution 46.

Thus, in use, the air supply 43 and the high voltage power supply 40 are activated, resulting in a flow of air passing from the air pump 43 via the flow control means 44 to the fluidiser 45. In the fluidiser 45, an aerosol of beads is produced which is then transferred to the treatment chamber 42 at which a corona discharge zone is generated between the high voltage electrode and the ground electrode. The aerosol of beads passes through the corona discharge zone where the beads are activated. Subsequently, the activated beads pass into the phage solution 46 where the phage are bound to the activated beads.

In some alternative embodiments of the present invention, the flow control means 44 is in direct fluid communication with the treatment chamber 42 as well as being in fluid communication with the fluidiser 45. Furthermore, in these embodiments, the fluidiser 45 is in fluid communication with the treatment chamber 42 such that the aerosol of beads is delivered to the treatment chamber 42 downstream of the corona discharge zone. In use of these embodiments, a flow of air passes from the flow control means 42 into the treatment chamber 42 and passes through the corona discharge zone where the air is activated. At the same time, air passes from the flow control means 44 to the fluidiser 45 and an aerosol of beads is delivered to the treatment chamber where it mixes with the activated air, which, in turn, activates the beads. As in the previous embodiments, the activated beads are then passed to the phage solution 46 where the phage bind to the beads. The advantage of this alternative embodiment is that it alleviates the problem of "bead welding" within the treatment chamber 42.

Figure 7:
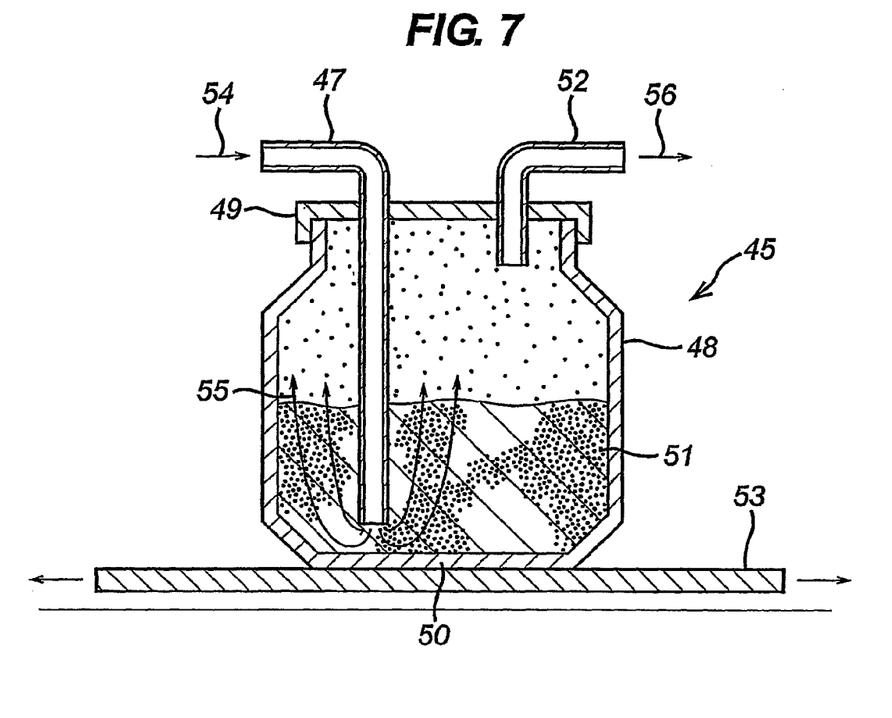
FIG. 7 is a cross-sectional view of a fluidiser in accordance with one embodiment of the present invention.

Referring to FIG. 7, an example of a fluidiser 45 will now be described in further detail. The fluidiser 45 comprises an air intake tube 47 which leads into a sealed vessel 48 through an aperture in the lid 49 of the sealed vessel. The air intake tube 47 leads vertically downwardly into the sealed vessel 48 almost to the base 50 of the vessel. The sealed vessel 48 is approximately half full of beads 51. Thus the air intake tube 47 terminates below the level of the beads 51. Also located in the lid 49 of the sealed vessel 48 is a vertically aligned outlet tube 52 which protrudes a short way into the top of the sealed vessel 48. Thus the outlet tube 52 terminates above the level of the beads 51. The sealed vessel 48 is located on a shaker table 53.

In use, air from the flow control means 44 is pumped into the air inlet tube 47 as shown by the arrow 54. The air is pumped beneath the level of the beads 51 and mixes with the beads 51, the mixture of air and beads subsequently escaping upwardly as shown by the arrows 55. Simultaneously, the shaker table 53 agitates the beads 51 so as to encourage the formation of an aerosol of the beads 51. The aerosol of beads then escapes via the outlet pipe 52 in the direction of the arrow 56 which leads to the treatment chamber 42. The aerosol thus generated by the action of the aeration and the mechanical agitation from the shaker table 53 is forced out of the sealed vessel 48 by the inflow of compressed air.

Figure 8:
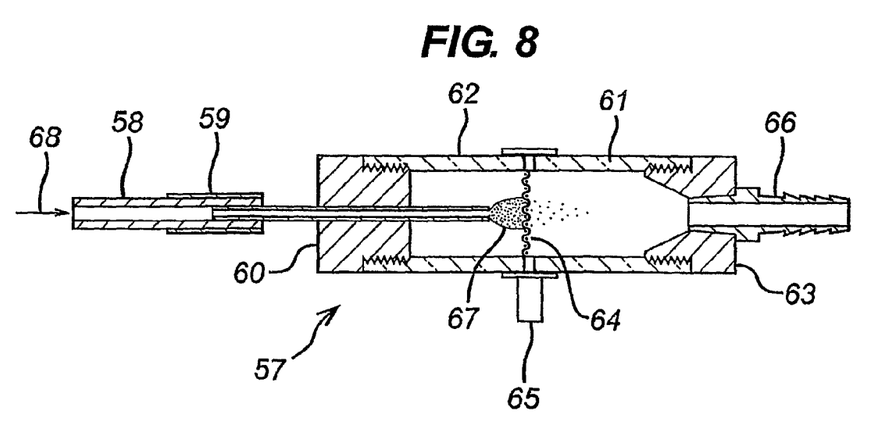
FIG. 8 is a longitudinal cross-sectional view of a treatment chamber in accordance with one embodiment of the present invention.

Referring to FIG. 8, one example of a treatment chamber 57 is shown. The treatment chamber 57 comprises an inlet tube 58 about which is located an annular high voltage electrode 59. The inlet tube 58 leads into a first end 60 of a generally cylindrical treatment compartment 61. The inner portion of the inlet tube 58 is made of a conducting material and therefore forms an extension of the high voltage electrode 59. The cylindrical sidewalls 62 of the treatment compartment 61 are made from perspex. Opposite the first end 60 of the treatment compartment 61 is a second end 63. Approximately halfway between the first and second ends 60, 63 is an earth mesh electrode 64 which is generally circular and which sits perpendicular to the axis of the treatment compartment 61. The earth mesh electrode is connected to an earth stud 65 which leads out of the sidewall of the treatment compartment 61. Leading out of the second end 63 of the treatment compartment 61 is an exit nozzle 66.

In use of the embodiment shown in FIG. 8, the high voltage power supply 40 is applied which results in a corona discharge zone 67 being generated between the inner end of the inlet tube 58 and the earth mesh electrode 64. An aerosol of beads enters the inlet tube 58 from the fluidiser 45, as shown by the arrow 68. The bead aerosol passes through the inlet tube 58 and the corona discharge zone 67 where the beads are activated. The activated beads then pass through the apertures in the earth mesh electrode 64 and leave the treatment compartment 61 via the exit nozzle 66 from where they pass to the phage solution 46 and bind to the beads.

Figure 10:
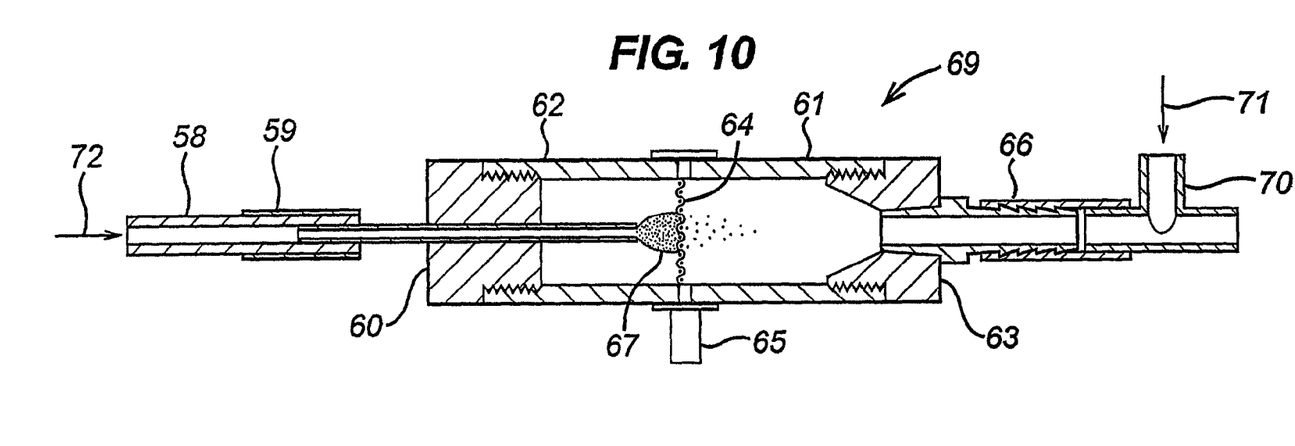
FIG. 10 is a longitudinal cross-sectional view of a treatment chamber in accordance with an alternative embodiment of the present invention.

Referring now to FIG. 10, an alternative embodiment of the treatment chamber will be described. In this embodiment, the treatment chamber 69 comprises many of the same components as the embodiment shown in FIG. 8 and like components are given like numbers. In this embodiment, the exit nozzle 66 additionally has a secondary intake 70 which mixes the efflux from the treatment compartment 61 with an aerosol of beads from the fluidiser 45, as shown by the arrow 71. Furthermore, instead of a bead aerosol entering the inlet tube 58, an air stream 72 enters the inlet tube 58. Therefore, in use, air enters the inlet tube 58 and passes through the corona discharge zone 67 where it is activated. Subsequently, the activated air passes through the earth mesh electrode 64 and leaves the treatment compartment 61 via the exit nozzle 66. It is then mixed with the bead aerosol which enters via the secondary intake 70. The activated air merges with the stream of aerosol beads and in turn activates the beads before passing the beads to the phage solution 46 where bacteriophage are bound to the beads.

Figure 11:
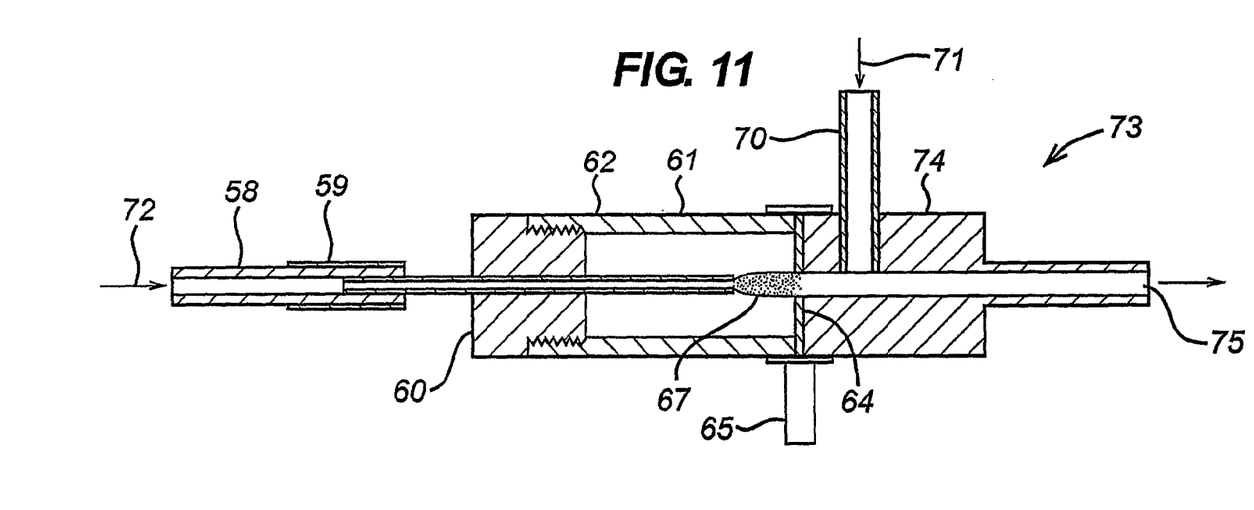
FIG. 11 is a longitudinal cross-sectional view of a treatment chamber in accordance with another alternative embodiment of the present invention.

Referring now to FIG. 11, a further embodiment of a treatment chamber will now be described. A treatment chamber 73 comprises many of the same components as the treatment chamber 69 depicted in FIG. 10 and like components are given like numbers. In this embodiment, the section of the treatment compartment 61 between the earth electrode 64 and the second end 63 is replaced with a PVC mixing nozzle 74. The mixing nozzle comprises an axial bore 75 which is aligned with the inlet tube 58. Furthermore, the secondary intake 70 leads through the PVC mixing nozzle 74 and into the axial bore 75 adjacent to the earth mesh electrode 64.

In use of this embodiment, an air stream enters the inlet tube 58 as shown by the arrows 72 and passes through the corona discharge zone 67 where the air is activated. The activated air then passes through the earth mesh electrode 64 and enters the axial bore 75 of the PVC mixing nozzle 74. Immediately after entering the PVC mixing nozzle 74, the activated air is mixed with a bead aerosol which enters the PVC mixing nozzle 74 via the secondary intake 70 as is shown by the arrow 71. The aerosol of beads is activated by mixture with the activated air and is then passed to the phage solution 46 where phage are bound to the beads.

Figure 12:
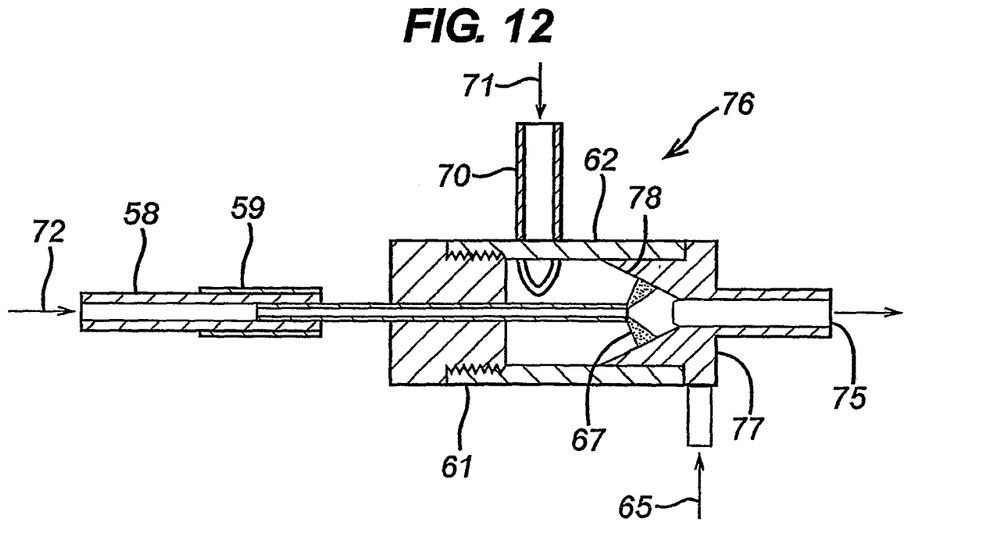
FIG. 12 is a longitudinal cross-sectional view of yet another alternative embodiment of a treatment chamber.
Figure 13:
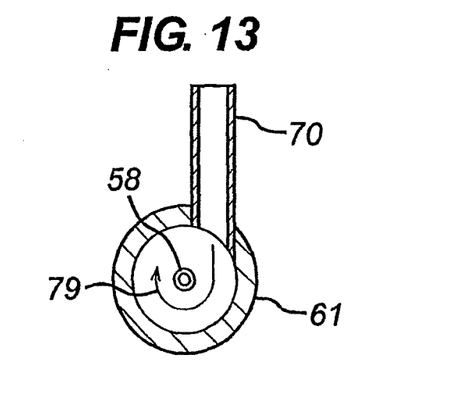
FIG. 13 is a lateral cross-sectional view of the treatment chamber depicted in FIG. 12.

Referring now to FIGS. 12 and 13, a further embodiment of a treatment chamber 42 will now be described. A treatment chamber 76 comprises many of the same components as the treatment chamber 73 depicted in FIG. 11 and like components are given the same numbers. In this embodiment, the secondary intake 70, rather than being located in the PVC mixing nozzle is instead located in the sidewall 62 of the treatment compartment 61 such that the secondary intake 70 leads into the treatment compartment 61 perpendicular to where the inlet tube 58 extends into the interior of the treatment compartment 61. Furthermore, in this embodiment, the mixing nozzle and the earth electrode are combined into a single electrode/mixing nozzle 77. As in the previous embodiment, the mixing nozzle 77 has an axially extending bore 75 which is aligned with the inlet tube 58. However, in this embodiment, the electrode/mixing nozzle 77 has a funnel shaped inlet 78, leading to the axially extending bore 75, from which the inner end of the inlet tube 58 is located a short distance away.

As is most easily seen in FIG. 13, the secondary intake 70 is offset so that its axis is not aligned with the axis of the treatment compartment 61.

In use of this embodiment, the high voltage power supply is activated, which results in a corona discharge zone 67 being generated between the inner end of the inlet tube 58 and the funnel shaped inlet 78 of the electrode/mixing nozzle 77. A supply of air enters the inlet tube 68 as is shown by the arrows 72. Simultaneously, an aerosol of beads passes in through the secondary intake 70 as is shown by the arrow 71. It is to be appreciated that the secondary intake 70, in this embodiment, is upstream of the corona discharge zone 67. Furthermore, because the secondary intake 70 is offset from the axis of the treatment compartment 61, the bead aerosol follows a helical path through the treatment compartment 61 as is shown by the arrow 79 in FIG. 13. The helical flow of bead aerosol then passes through the corona discharge zone 67 where the beads are activated and mix with the air from the intake 58. The activated beads then pass to the phage solution 46 where they mix and the bacteriophage bind to the beads.

In some further embodiments of the present invention, a plurality of treatment chambers are provided, linked together in series so as to increase the exposure time of the beads to an electrical discharge. For example, in one embodiment, a first treatment chamber 57 is provided as shown in FIG. 8. However, instead of the exit nozzle 66 leading to phage solution 46 it instead leads to a second treatment chamber 57 substantially identical to the first treatment chamber. The exit nozzle 66 of the second treatment chamber 57 leads to the phage solution 46. In use, the bead aerosol passes through the first treatment chamber 57 as described above and the beads are activated by the corona discharge in the first treatment chamber 57. Subsequently, the bead aerosol passes through the second treatment chamber 57 and the beads are further activated by the corona discharge in the second treatment chamber 57. The advantage of this embodiment is that a higher level of activation of the beads is achieved which results in a higher level of binding of the bacteriophage to the beads. It is to be understood that, while in this embodiment only two treatment chamber are provided, in other embodiments three or more treatment chambers are provided.

The above described embodiments relate to the binding of bacteriophage to beads. However, it is to be understood that in other embodiments of the present invention other virions (i.e. virus particles) are bound to particulate materials which are not bead-shaped.

EXAMPLES

Example 1

Method 10 micron nylon beads were exposed as a monolayer to corona discharge of 60 KVa for 0.1 seconds using a motorised bed corona discharge system (Sherman Treaters Laboratory motorised treatment system). 10 ml of bacteriophage suspension ($10^8$ bacteriophages per ml) was added to the beads within 1 minute of treatment.

Beads were left for several hours then removed from the bacteriophage suspension by vacuum filtration through a glass fibre filter. Beads were washed with distilled water (5 ml) five times and the filtrate was tested for free (unbound) bacteriophages.

For free bacteriophage determination 900 μl of filtrate was treated by centrifugation at 10,000 g for 5 minutes and filtered through a 0.22 micron filter before plating in a standard plaque assay with MRSA 15 (Methicillin resistant *Staphylococus aureus*) as the test organism.

For the bound bacteriophage determination, beads after washing were placed on agar plates in a standard plaque assay with MRSA 15 as the test organism. Serial dilutions were used.

Beads with bound bacteriophages were allowed to dry at room temperature and left for 1 week, with samples taken at intervals for activity testing.

Results

The results of the determination of the amount of bacteriophage bound to the beads are shown in FIG. 4.

The results of the determination of the amount of bacteriophage removed by washing are shown in FIG. 5.

The results of determination of bound bacteriophage activity over time are shown in Table 1.

TABLE 1

| Time (days) | Number of plaques at $10^{-2}$ dilution | Number of plaques from unbound bacteriophages under same conditions |
|---|---|---|
| 0 | 13 | 15 |
| 1 | 12 | 0 |
| 2 | 12 | 0 |
| 7 | 0 | 0 |

Conclusions

Bacteriophages were immobilised onto nylon beads following corona discharge treatment of the bead surfaces. These bacteriophages were strongly bound so that they are not removed by repeated washings.

The bacteriophage coated beads retained their activity for at least 48 hours after dehydration.

Example 2

Experiments were carried out to test treatment chambers for corona treatment of nylon beads with nominal diameters of 10 μm. The experimental set up allowed the generation of corona of both polarities. The generation of corona plasma occurs when the electric field strength is sufficient to act on an initiating electron creating an ionisation avalanche in the gas surrounding the high voltage electrode. The voltage required to generate corona depends on the polarity, the geometrical proportions of the electrode arrangement, the gas type and the pressure.

Figure 5:
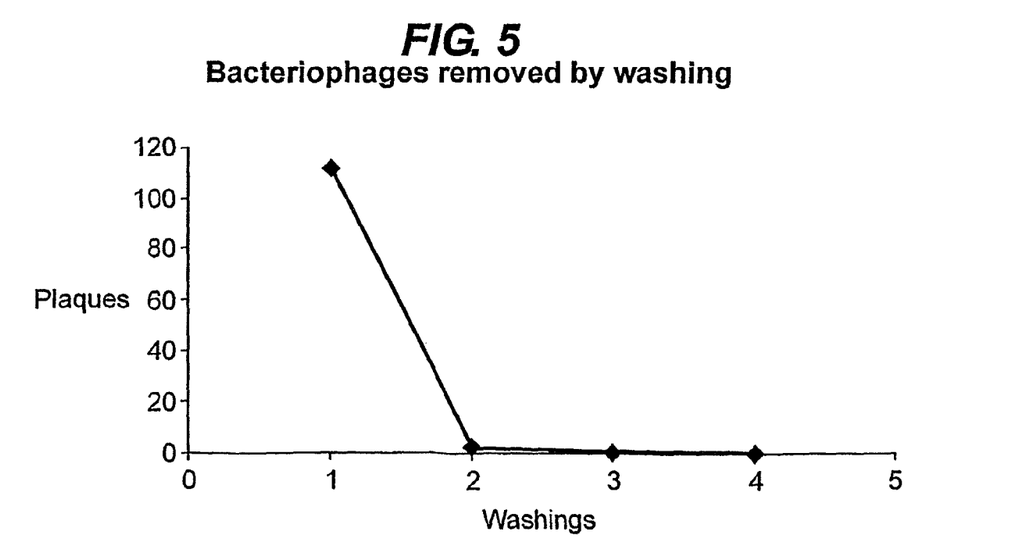
FIG. 5 is a graph showing the determination of the amount of bacteriophage removed from beads by washing after the beads have been treated by a method in accordance with one embodiment of the present invention.

In this example, testing was carried out using an apparatus as shown in the block diagram of FIG. 6 wherein the fluidiser was that shown in FIG. 5 and the treatment chamber was that shown in FIG. 8. The treatment chamber was designed to pass the aerosol stream through the annular high voltage electrode 59 where it would exit directly into the region of corona generation 67. It was anticipated that this method would maximise the exposure of the beads to the corona. The results are shown in Table 2.

Figure 9:
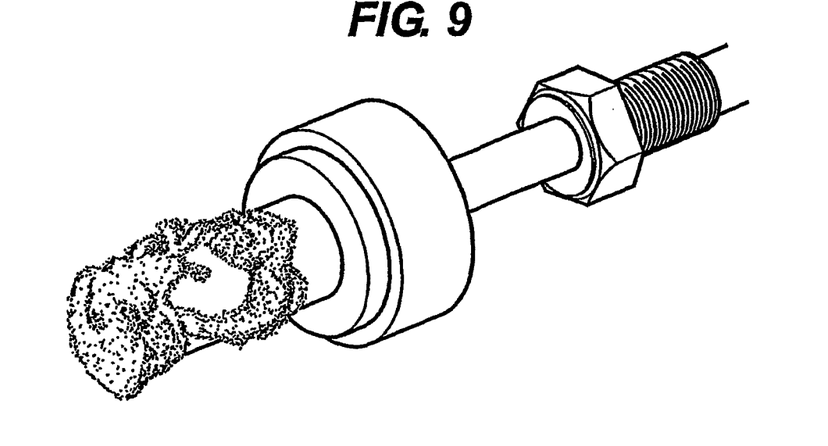
FIG. 9 is a photograph of a component of a treatment chamber as shown in FIG. 8, after several minutes use.

During testing, an unforeseen consequence arose wherein the beads tended to be welded to the mesh electrodes 64. After several minutes of running, this effect caused a fused mass to bridge the gap between the electrodes rendering the chamber inoperative. A photograph of the resulting fused mass is shown in FIG. 9. In addition to the spray welding problem, another issue which arose was the clogging of the chamber with beads that had settled out of the aerosol. During operation, the beads would tend to be dispersed around the inside of the chamber, remaining attached, presumably through electrostatic adhesion.

Example 3

The experiment of Example 2 was repeated but with a treatment chamber as shown in FIG. 10, wherein a separate air stream from the flow control means 44 was directed by the inlet tube 58 and the aerosol from the fluidiser 45 entered via the secondary intake 70. The results are shown in Table 2. This configuration eliminated the bead welding problem.

Example 4

In this Example, the experiment of Example 3 was repeated but using the treatment chamber as shown in FIG. 11. In this design, an air stream entered the high voltage electrode 59, emerging into the region of corona generation 67 where it carried active species from the corona into the mixing nozzle 74. The stream then merged with the bead aerosol and continued on to the phage solution. The results are shown in Table 2. This design prevented any bead welding, as well as eliminating the clogging of the chamber.

Example 5

It was thought that the activation level of the beads could be increased by increasing the exposure time of the beads to the corona discharge. Therefore, in this example, the experiment of Example 4 was repeated but substituting the treatment chamber shown in FIGS. 12 and 13. More specifically, a vortex arrangement was implemented in order to increase the exposure time wherein the beads entered the chamber tangentially and were then forced to follow a helical path through the corona. The high voltage power supply range was also changed in favour of a pulsed output. This was done to try and distribute the corona discharge around the electrode so as to expose the aerosol better. The results are shown in Table 2. This chamber suffered from clogging although there was no evidence of bead welding.

TABLE 2

| Example | Chamber (Figure No.) | Polarity | Plates | Wash |
|---|---|---|---|---|
| 2 | 8 | +ve | 0 Plaques | 0 |
| 2 | 8 | −ve | 4 Plaques | 0 |
| 3 | 10 | +ve | NULL[1] | NULL |
| 4 | 11 | +ve | 3 Plaques | 0 |
| 4 | 11 | −ve | NULL[2] | NULL |
| 5 | 12 | Pulsed +ve | 0 | 0 |
| 5 | 12 | Pulsed +ve | 4 | 0 |

[1] For this test there was too much free phage present to wash off in a reasonable number of wash cycles, so it was not possible to determine if the beads had immobilised any phage.
[2] There was insufficient sample in this test for more than one wash - plating the sample and the first wash produced plaques on both, however there was not enough sample remaining for further wash cycles.

The invention claimed is:

1. A method of binding virions to a plurality of particles comprising the steps of:
    (a) attracting the particles to a conveyor, which attracting comprises charging the conveyor so as to attract the particles to the conveyor, and moving the conveyor in order to bring the particles into proximity with an electrical discharge;
    (b) then using the electrical discharge in order to activate the particles; and
    (c) mixing the activated particles with the virions such that the virions become bound to the particles.

2. A method according to claim 1, wherein step (b) comprises the step of exposing the particles to the electrical discharge.

3. A method according to claim 1, wherein step (b) comprises the step of exposing a medium to the electrical discharge and mixing the medium with the particles.

4. A method according to claim 1, wherein a portion of the conveyor is in contact with a source of the particles.

5. A method according to claim 1, wherein step (b) comprises reversing the charge on the particles and removing the particles' attraction to the conveyor.

6. A method according to claim 1, wherein the conveyor comprises a rotatable drum.

7. A method according to claim 1, wherein the conveyor comprises a movable conveyor belt.

8. A method according to claim 3, wherein the medium is a gas.

9. A method according to claim 8, wherein the gas is selected from the group consisting of oxygen, and air.

10. A method according to claim 8, wherein the gas is inert.

11. A method according to claim 1, wherein the particles are mixed with the virions in a solution.

12. A method according to claim 11, and further comprising the step (c) of extracting the particles from the solution.

13. A method according to claim 1, wherein the particles are beads.

14. A method according to claim 1, wherein the virions are bacteriophage.

15. A method according to claim 1, wherein the electrical discharge is a pulsed corona discharge.

16. A method according to claim 10, wherein the gas comprises nitrogen.

17. A method according to claim 13, where the beads are nylon beads.

* * * * *